United States Patent [19]
Runciman et al.

[11] Patent Number: 5,651,283
[45] Date of Patent: Jul. 29, 1997

[54] BONE PLATE SHAPING DEVICE

[75] Inventors: John Runciman, Renfrew; Raymond Desjardins, White Lake, both of Canada

[73] Assignee: Terray Corporation, Arnprior, Canada

[21] Appl. No.: 559,246

[22] Filed: Nov. 16, 1995

[30] Foreign Application Priority Data

Nov. 14, 1995 [CA] Canada ................ 2162837

[51] Int. Cl.$^6$ ................ B21D 9/08
[52] U.S. Cl. ............ 72/390.4; 72/390.5; 72/404; 72/409.01; 72/409.13
[58] Field of Search .......... 72/472, 404, 409.01, 72/409.05, 409.13, 390.4, 390.5

[56] References Cited

U.S. PATENT DOCUMENTS

| | | |
|---|---|---|
| 951,717 | 3/1910 | Andres . |
| 1,108,493 | 8/1914 | Federespiel ............ 72/409.01 |
| 1,409,835 | 3/1922 | Doble ............ 72/409.01 |
| 1,479,762 | 1/1924 | Wagenbach . |
| 1,842,678 | 1/1932 | Kreuzeder ............ 72/409.01 |
| 2,087,125 | 7/1937 | Smith et al. . |
| 2,252,891 | 8/1941 | Heinrich ............ 72/409.01 |
| 2,502,713 | 4/1950 | Fagge . |
| 3,244,201 | 4/1966 | Wallshen ............ 72/390.5 |
| 3,357,460 | 12/1967 | Gawura ............ 72/409.13 |
| 3,709,264 | 1/1973 | Amman . |
| 3,747,648 | 7/1973 | Bauer ............ 72/409.01 |
| 3,824,834 | 7/1974 | Durham . |
| 3,901,064 | 8/1975 | Jacobson . |
| 4,041,740 | 8/1977 | Villazon ............ 72/409.01 |
| 4,091,845 | 5/1978 | Johnson . |
| 4,132,100 | 1/1979 | Schuler . |
| 4,304,117 | 12/1981 | Rawson . |
| 4,373,373 | 2/1983 | Schaefer ............ 72/409.01 |
| 4,474,046 | 10/1984 | Cook . |
| 4,691,555 | 9/1987 | Vaughan . |
| 4,716,757 | 1/1988 | McGregor et al. . |

(List continued on next page.)

FOREIGN PATENT DOCUMENTS

| 10650 | 3/1908 | Denmark . |
|---|---|---|
| 479753 | 8/1929 | Germany . |

OTHER PUBLICATIONS

"New Pelvic Plates for internal fixation of acetabular and pelvic fractures", product brochure, Zimmer, Inc., 1983, 4 pgs.

"LUQUE Segmental Spinal System Instruments", catalog extract, Zimmer, Inc., 1987, p. D32 plus back cover.

"General Instruments", catalog extract, Zimmer, Inc., 1987, p. D59–D61 plus back cover.

"Electrical Bone Growth Stimulation", catalog extract, Zimmer, Inc., 1987, p. H86 plus back cover.

"INTRAFLEX Intramedullary Pins" and Rush Pins, catalog extract, Zimmer, Inc., 1987, p. B66 and B70–71 and back cover.

"Instruments for Plate Fixation", catalog extract, Synthes, Aug., 1992, pp. 3–24 and 3–25.

"Richards L–Rod System", catalog extract, Richards, dated prior to Nov. 14, 1995, p. L–5.

"2400–83 Hand Bender", 2400–36 French Rod Bender, 2400–37 3/16 Adapter, French Rod Bender, 2400–38 Rod Cutter, Large, catalog extract, DEPUY, dated prior to Nov. 14, 1995, 1 page.

*Primary Examiner*—David Jones
*Attorney, Agent, or Firm*—Pearne, Gordon, McCoy & Granger LLP

[57] ABSTRACT

A device for contouring bone plates is described. The device has a first handle and a first jaw extending from a first end of the first handle. A second jaw is hinged at one end of the region of the junction of the first handle and first jaw, a second handle is hinged at one end to the second jaw between the ends of the second jaw. A strut is hinged to the second handle between the ends thereof, and extends to the first handle. The first and second jaws are provided with at least one set of complementary surfaces for contouring a bone plate.

26 Claims, 4 Drawing Sheets

U.S. PATENT DOCUMENTS

| | | |
|---|---|---|
| 5,013,314 | 5/1991 | Firica et al. . |
| 5,084,935 | 2/1992 | Kalthoff ............................ 72/409.01 |
| 5,161,404 | 11/1992 | Hayes . |
| 5,290,281 | 3/1994 | Tschakaloff . |
| 5,354,301 | 10/1994 | Castellano . |
| 5,373,860 | 12/1994 | Catone . |
| 5,389,099 | 2/1995 | Hartmeister et al. . |

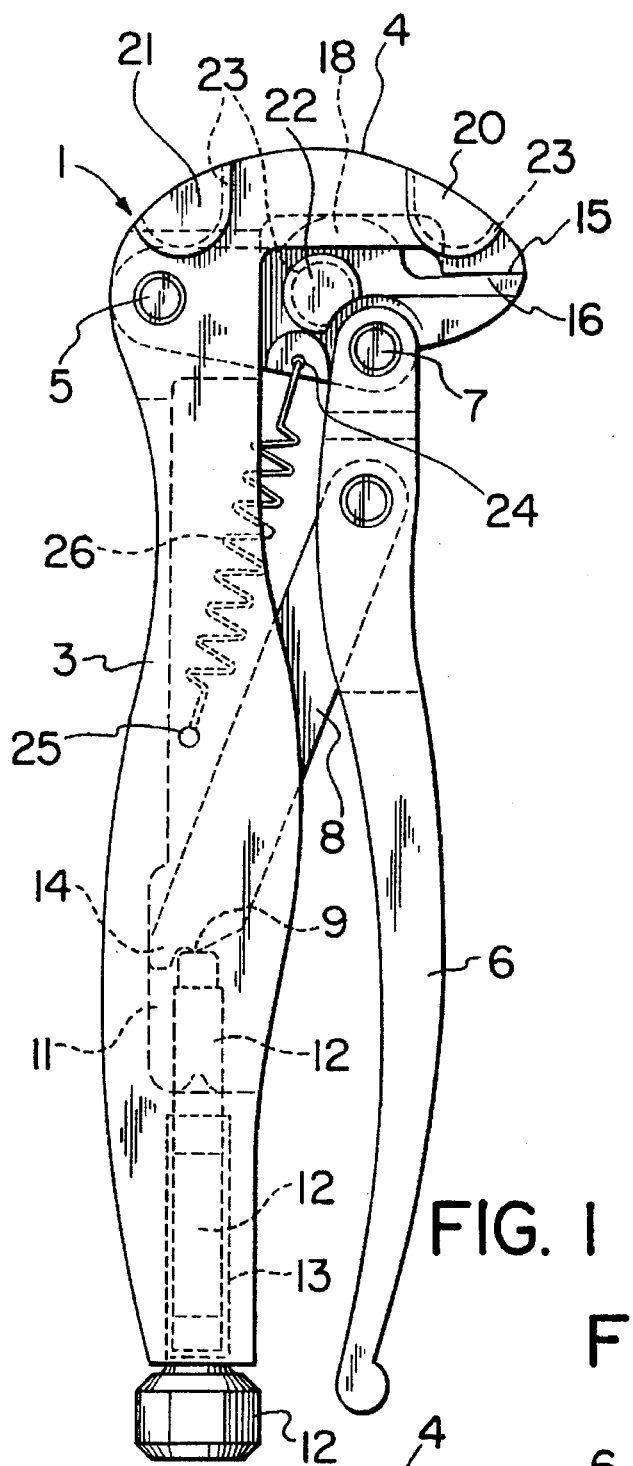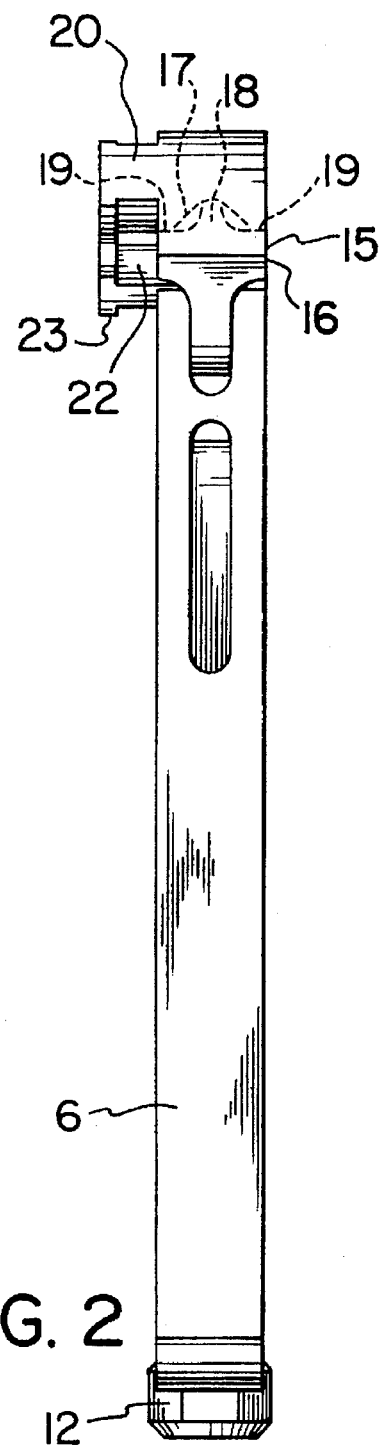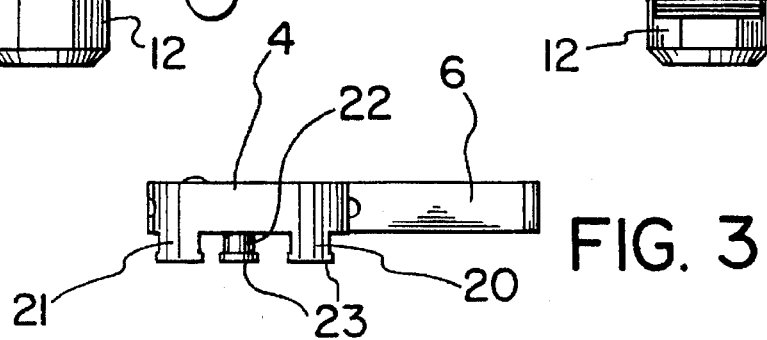

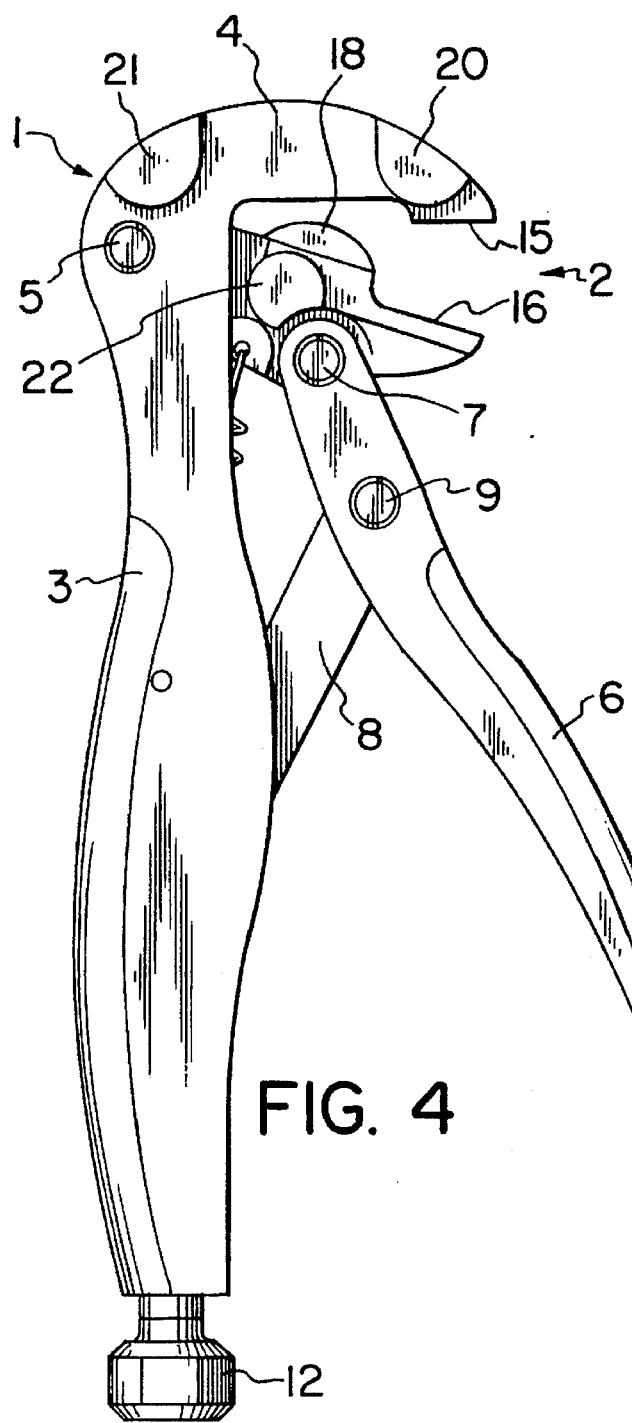
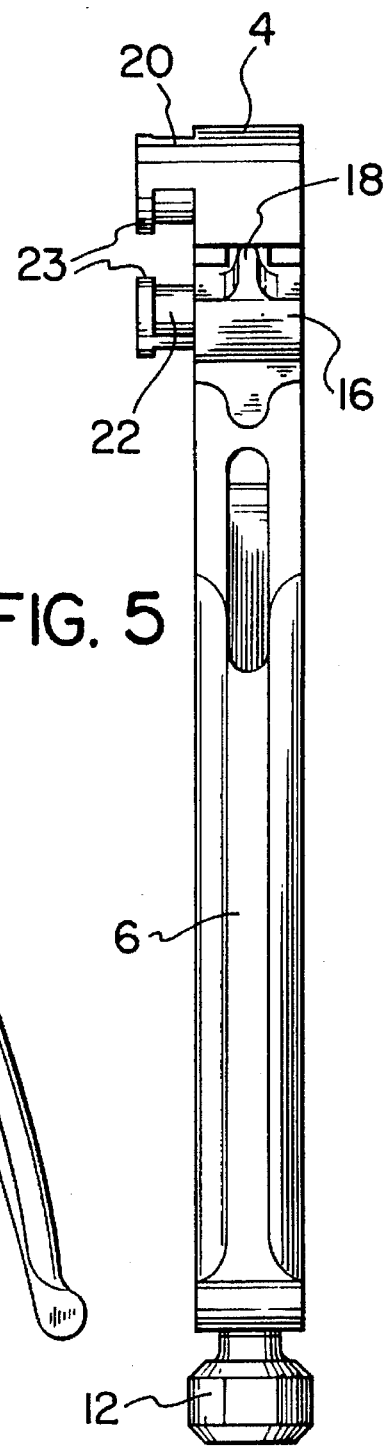
FIG. 4
FIG. 5

BONE PLATE SHAPING DEVICE

The present invention relates to the field of surgical instruments. In particular, the present invention provides a device for bending, arcing, twisting and otherwise shaping orthopaedic reconstruction plates.

An orthopaedic reconstruction plate (often called a bone plate) is a metallic plate, usually made from stainless steel, that is configured and adapted for attachment to bone surfaces, across fractures or areas of reconstruction, to compress and immobilize those cites, and thereby assist in the rebuilding and mending thereof of the bones to which they are attached. Typically, a bone plate is an elongated strip, apertured at regular intervals for insertion of surgical screws therethrough. The surfaces of the strip may be contoured, textured or otherwise formed to assist in their proper and secure placement on a bone surface.

It will be appreciated that the surface of the bone is rarely flat or straight. Therefore, it is necessary in most instances to alter the shape of the bone plate by arcing, bending or twisting, or a combination thereof, to make the plate conform to the surface of the bone, or to the shape the surgeon desires to make the bone assume through the use of the bone plate.

In this specification, arcing shall refer to changing the shape of an elongate bone plate in a direction parallel to the planes of the upper and lower surfaces of the bone plate. Bending is changing the shape of a bone plate in a direction perpendicular to the planes of the upper and lower surfaces thereof. Twisting is changing the shape of a bone plate rotationally with respect to the planes of the upper and lower surfaces thereof. In each case, the bone plate is considered to have flat, parallel upper and lower surfaces, even though in reality, this is not necessarily the case.

There currently exist a number of instruments to assist a surgeon in shaping a bone plate in the ways described above, or combinations of those ways. The most common plate shaping instruments are bending irons. These are simple elongated bars, slotted at each end to accept a particular plate. The surgeon, using two such irons slipped over a plate, spaced apart as required, can exert a large amount of torque or bending moment on a plate. These irons cannot be used for arcing.

Arcing has been an especially difficult task for a surgeon attempting to achieve a perfect fit of a bone plate during an operation. It will be understood that the amount of force required to be exerted to achieve arcing of a bone plate is considerable, and so this has been a job generally done in advance with the use of X-rays.

Other instruments and methods for shaping bone plates include specially adapted pliers, and bench-mounted bending presses that will bend a plate between a pair of anvils, one anvil having a single contact point, and the opposite anvil having a spaced pair of contact points, whereby bringing the anvils together with a plate between then results in a three point bending load, the single anvil bending the plate into the shape between the two spaced apart anvils.

It is an object of the present invention to provide a surgical tool that can be used by a surgeon to arc, bend, or (using a pair of tools) twist a bone plate with a minimum of effort, and a maximum of control.

A further object of the present invention is to provide a single tool for use by a surgeon to either bend or arc bone plates, as required.

Yet a further object of the present invention is to provide a tool with a capability of locking pliers to permit a surgeon to grasp a bone plate with one hand, and perform manipulations or modifications on it with the other, with the assurance that the bone plate will not slip or otherwise come free from the surgeons grasp.

In a broad aspect, the present invention relates to a device for shaping or contouring bone plates or malleable strips of metal, said device having a first handle, a first jaw extending from a first end of said first handle, a second jaw hinged at one end in the region of the junction of said first handle and first jaw, a second handle hinged at one end to said second jaw between the ends of said second jaw, a strut hinged to said second handle between the ends thereof, and extending to said first handle; said first and second jaws being provided with at least one set of complementary surfaces for contouring a said malleable strip of metal.

In drawings that illustrate the present invention by way of example:

FIG. 1 is a side view, partly in phantom, of a bone plate shaping tool according to the present invention;

FIG. 2 is a front view thereof;

FIG. 3 is a top view thereof, with the jaws in the open state;

FIG. 4 is a side view thereof, with the jaws in the open state;

FIG. 5 is a front view thereof, with the jaws in the open state;

Figure 6A:
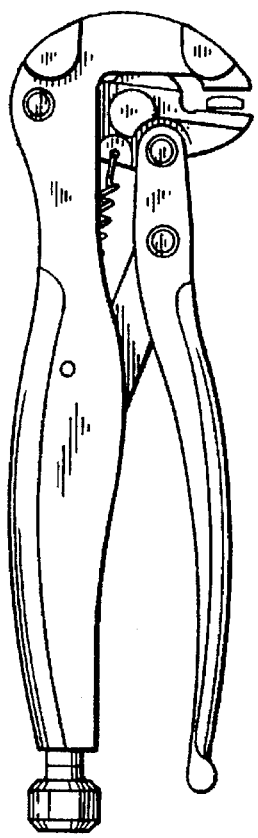
FIGS. 6A and 6B are side views of the tool of the present invention gripping a bone plate in a first way.

Referring now to the drawings, the present invention provides a bone plate shaping device indicated generally at 1. It includes an inner handle 3, from the upper end of which extends an upper jaw 4. As illustrated, the upper jaw may extend generally normal to the inner handle 3, but it will be understood that the angle between the upper jaw 4 and the inner handle may be substantially greater or less than 90°, from about 30° to about 150°.

A lower jaw 2 is pivotally connected to the upper jaw 4 at a first hinge point 5 that is at the point of transition between the inner handle 3 and the upper jaw 4. It will be understood that the hinge point may be constructed in any suitable manner, and the exact manner of construction will be a matter of choice to one skilled in the art. In the device illustrated, the inner extent of the lower jaw is formed as a tang insertable into a slot in the inner handle. A transversely extending aperture and the tang of the jaw 2 and in the handle, at hinge point 5 accommodates a hinge pin.

The lower jaw is lightly tensioned toward an open position by means of a tension spring 26 extending between attachment points 24 and 25 on the lower jaw 2 and inner handle 3 respectively (see FIG. 1). The lower jaw is tensioned toward the open position in order to provide a constant positive grip for a surgeon as the surgeon manipulates the device.

Around the middle of the lower jaw 2, a second pivot point 2 is provided between the lower jaw 2 and an outer handle 6, that extends generally downwardly from the lower jaw. The second pivot point is constructed similarly to the first, with the lower jaw 2 slipping into a slot formed into the upper end of the handle 6, and a pin being inserted in an aperture formed at that point. Again, it will be understood that the hinge point may be constructed in any manner selected by one skilled in the art.

A third hinge point 9 is provided on the outer handle 6, slightly down from the second hinge point 7, between the outer handle and a strut 8 that extends between the outer handle 6 and the strut 8. The third hinge point is formed like the first, with the end of strut 8 accommodated in a slot formed in the outer handle, and a pin being inserted in an aperture formed in the outer handle and strut at hinge point 9. It will be understood that any other suitable hinge construction may be utilized at that point.

The other end of the strut 8 extends to the inner handle 1. Inner handle 1 has a threaded bore 13 formed in the lower end thereof, and a threaded adjustment bolt 12 is contained within that bore. Bolt 12 terminates at its upper end in a channel 11 formed in the inner handle. Strut 8 extends into that channel 11, the end 14 of strut 8 projecting somewhat and being flattened to bear against the wall of the channel 11, just behind the end of bolt 12. The end 9 of the strut 8 where it contacts the bolt 12 is rounded, whereby smooth contact between the strut and the end of bolt 12 is assured as the bolt is rotated to move longitudinally, or as the strut is pivoted by the opening of the outer handle 6.

Given the handle and jaw relationship detailed above, it will be understood that the handle of the present device functions in much the same way as a locking plier (but without the locking function). That is, as the adjustment bolt is adjusted downwardly, the strut moves down, and the fully closed position of the device will be with the jaws open. Moving the adjustment bolt up provides a fully closed position with the jaws closed. Any position between the two is possible or desirable depending on the use being made of the device, and the size of the surgeon's hands.

Figure 6B:
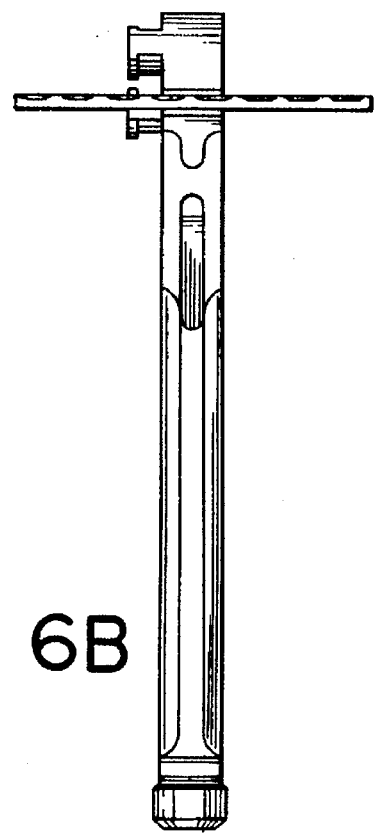

The jaws 2, 3 of the device are provided with three distinct gripping/contouring functions. At their outermost extremities, the upper 4 and lower 2 jaws are provided with flat gripping surfaces 15,16 that can be squeezed together, with a bone plate held between them, to provide a very firm grip on the bone plate as shown in FIGS. 6A and 6B. Gripping a bone plate at two points with two devices according to the present invention, or with one device according to the present invention, and a second conventional device such as a bench mounted vise or a bending iron, will permit a surgeon to twist the plate. Moreover, the ability to twist the plate utilizing the present invention will be enhanced over the use of bending irons or pliers alone. Bending irons, by their nature, are slotted for insertion of a bone plate, so twisting the bone plate can cause the iron to slip off the end of the plate. Pliers, on the other hand, are simple levers, and so require constant exertion of great force during the twisting procedure, and therefore they are of limited value in twisting a bone plate. The present invention however, with its compound lever arrangement, brings the upper part of the outer handle, and the strut into a near straight line relationship, beneath the lower jaw. Maintaining that straight-line support of the lower jaw requires only minimal force of the outer handle 6.

Figure 7A:
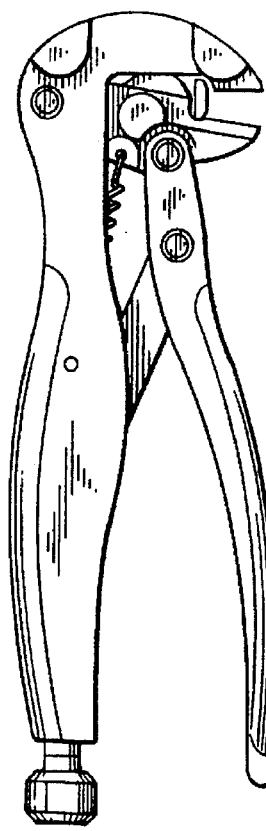
FIGS. 7A and 7B are side views of the tool of the present invention gripping a bone plate in a second way.
Figure 7B:
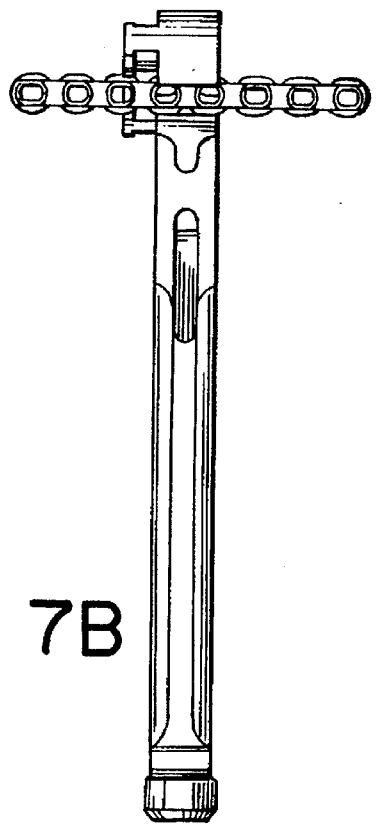

Moreover, as shown in FIGS. 7A and 7B, a bone plate can alternatively be gripped on its side, in the small space formed behind the gripping surface 15 of the upper jaw 4.

Just behind the gripping surface of the upper jaw is formed a groove 17, flanked by a pair of bearing surfaces 19. In the lower jaw there is formed a complementary tongue or ridge structure 18, that fits into groove 17. It will be understood that the structures provided on the upper and lower jaw may be interchanged. That is, the groove, and bearing surfaces may be provided on the lower jaw, and the tongue on the upper jaw. Such a modification will be easily made by one skilled in the art.

Figure 8A:
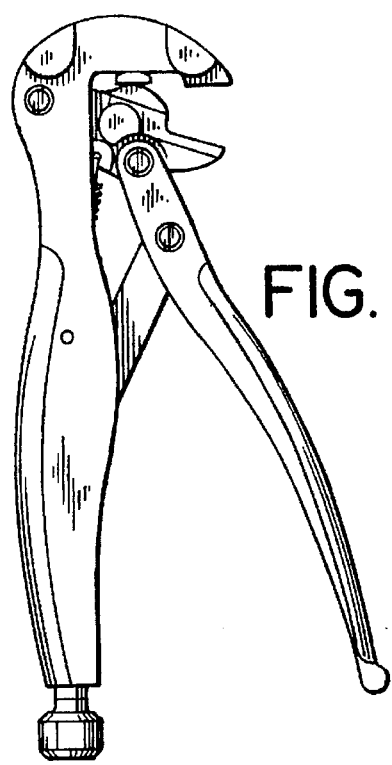
FIGS. 8A and 8B are side views of the tool of the present invention gripping a bone plate in a third way.
Figure 8B:
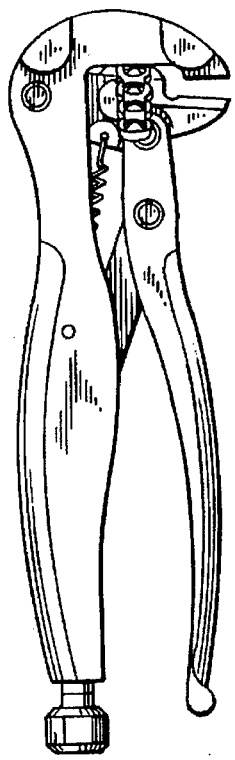

In order to use the tongue and groove bending structures provided, a plate is aligned between the tongue 18 and groove 17, at the point at which the plate is to be bent. The jaws are then forcibly closed, causing the tongue 18 to push the plate into the groove 17, whereby a three point bending load is applied to the plate by the tongue and the bearing surfaces 19. This is illustrated in FIGS. 8A and 8B. Pressure is released when the extent of bending required is achieved.

It will, moreover, be understood that the bending forces that can be generated using the compound lever arrangement of the handle structure of the present invention are quite great. Normally, the power exerted by a lever on a load is determined by the ratio of the relative distances between the load and fulcrum on the one hand, and the force and the fulcrum on the other. In the present case, the force to close the lower jaw will benefit from a first lever defined by the force on the inner handle 3, the fulcrum 5 and the load on the upper jaw; a second lever defined by the load on the outer handle, at point 7 and the distance from that point to fulcrum 9, and the distance then down the handle 6 to where the surgeon will apply force; and a third lever on the lower jaw defined by the relative distances between the force on the lower jaw, exerted at point 7, and the fulcrum 5 and the load on the lower jaw, exerted at 18, 22, or 16, there being a favourable ratio in the case of load at points 18 or 22, each of which is closer to pivot 5 than force point 7. The force exerted at point 7 will, moreover, be optimally directed by the rotation inwardly of strut 8, as handle 6 is squeezed, resulting in a concentration of force upwardly, rather than outwardly.

The device of the present invention is also provided, extending laterally outwardly from at least one of its two sides, with a set of three arcing anvils 20, 21, 22. These comprise spaced-apart front and rear upper anvils 20,21 that extend laterally from the upper jaw 4, and centrally located middle anvil 22 that extends laterally from the lower jaw 2.

Figure 9A:
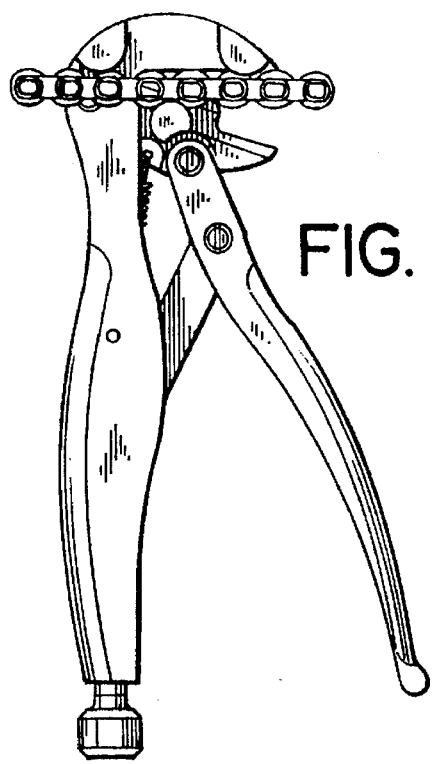
FIGS. 9A and 9B are side views of the tool of the present invention gripping a bone plate in a fourth way.
Figure 9B:
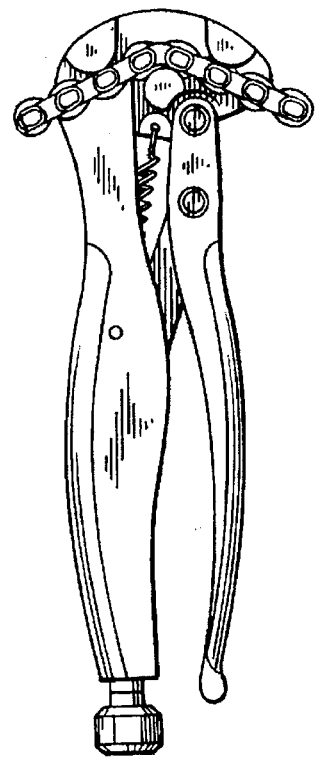

When the jaws are in a closed position, the anvil 22 of the lower jaw assumes a position generally between the two anvils 21, 20 of the upper jaw. When open, the lower anvil swings away from the upper anvils, creating a large gap into which can be inserted a bone plate, for lateral bending, or arcing. The arcing operation is shown in FIGS. 9A and 9B.

The outermost end of each laterally extending anvil is capped by a flange 23, the function of which is to ensure that the plate does not slip off the anvil while being arced. It will be noted that the lateral anvils are shown in a two upper-one lower configuration. In this regard, it will be understood that provision of two lower (at the ends) and one upper anvil will function well. Furthermore, a second set of anvils may be provided extending from the opposite side of the device, for instance to effect more or less curvature in a plate, through the provision of anvils spread further apart, or closer together.

It is to be understood that the examples described above are not meant to limit the scope of the present invention. It is expected that numerous variants will be obvious to the person skilled in the field of to which the present invention pertains without any departure from the spirit of the invention. The appended claims, properly construed, form the only limitation upon the scope of the invention.

We claim:

1. A device for contouring elongate bone plates that have lengths, widths and thicknesses, said device having a first handle, a first jaw extending from a first end of said first handle, a second jaw hinged at an inner end thereof in the region of the junction of said first handle and first jaw, a second handle hinged at one end to said second jaw between the ends of said second jaw, a strut hinged to said second handle between the ends thereof, and extending to said first handle; wherein a selected one of said jaws has a longitudinally extending groove formed therein, flanked by bearing surfaces, and the other one of said jaws is provided with a longitudinally extending ridge aligned with and opposed to said groove, said groove and ridge being dimensioned so that said groove accommodates said ridge when said jaws are closed, said ridge and said bearing surfaces flanking said groove functioning as opposed loading points to apply a three point bending load on a said bone plate placed therebetween, upon closure of said jaws; and wherein said bearing surfaces flanking said groove are spaced apart from one another by a distance sufficient to permit bending of a said bone plate into said groove, by said ridge.

2. The device as claimed in claim 1, wherein said ridge has a rounded upper profile, viewed from the front.

3. The device as claimed in claim 1, wherein said ridge has a rounded profile, viewed from the side.

4. The device as claimed in claim 1, wherein said jaws are provided with flat opposed grasping surfaces forward of said aligned and opposed groove and ridge.

5. The device as claimed in claim 4, wherein said grasping surfaces extend inwardly from the end of said jaws a distance at least about the width of a selected said bone plate.

6. The device as claimed in claim 5, wherein one of said gripping surfaces is slightly shorter than the other, whereby a space is created toward the inner ends of said jaws between the longer gripping surface, and the opposite jaw inward of the shorter gripping surface for the gripping of a said bone plate oriented on its side.

7. The device as claimed in claim 1, wherein one of said jaws is provided with a pair of bending anvils extending laterally from one side of the device, one of said pair of anvils being located near each end of said one jaw, and the other said jaw is provided with a single anvil extending laterally from the same side of the device, between the pair of anvils extending from the one jaw.

8. The device as claimed in claim 7, wherein each said anvil has a rounded surface in the direction facing the interior of the jaw.

9. The device as claimed in claim 8, wherein each anvil is capped with a short, round flange, the distance between a flange and the jaw defining the working depth of an anvil and being about equal to the thickness of a selected bone plate.

10. The device as claimed in claim 7, wherein a pair of said anvils is provided extending laterally from said first jaw, and a single said anvil is provided extending laterally from said second jaw.

11. The device as claimed in claim 7 wherein each side of each jaw has anvils extending therefrom, whereby two sets of anvils are provided, each having different contouring characteristics.

12. The device as claimed in claim 7, wherein each of at least two of said bending anvils is nonrotatably attached to the jaw from which it extends.

13. The device as claimed in claim 1, wherein the end of said strut extending to said first handle terminates in a downwardly directed rounded bearing surface.

14. The device as claimed in claim 13, wherein the lateral surface of said strut facing said first handle, and adjacent to said downwardly directed bearing surface is flattened from side to side, and rounded to bear against the surface of said first handle.

15. The device as claimed in claim 13, wherein said first handle has a channel formed therein to accommodate the end of said strut.

16. The device as claimed in claim 15, wherein the end of said first handle remote from said first jaw is provided with a threaded bore that accommodates an adjustment bolt the upper end of which is shaped to permit the end of said strut to seat against it.

17. The device as claimed in claim 16, wherein said adjustment bolt includes a head portion extending from the end of said first handle whereby the point of contact between said strut and said first handle, and thereby the closure of said jaws, can be adjusted by a person using the device.

18. The device as claimed in claim 1, including a tension spring between said second jaw and said first handle, to bias said jaws lightly to the open position.

19. The device as claimed in claim 1, wherein the said bone plate is a malleable strip of metal.

20. The device as claimed in claim 1, wherein said ridge has a base, each of said bearing surfaces sloping away at an angle from the base of said ridge.

21. The device as claimed in claim 20, wherein each of said bearing surfaces slopes away from the base of said ridge at the same angle.

22. The device as claimed in claim 1, wherein said longitudinally extending ridge terminates remotely from the distal end of the jaw on which it is provided.

23. A device for contouring bone plates, said device having a first handle, a first jaw extending from a first end of said first handle, a second jaw hinged at one end in the region of the junction of said first handle and first jaw, a second handle hinged at one end to said second jaw between the ends of said second jaw, a strut hinged to said second handle between the ends thereof, and extending to said first handle, said first and second jaws being provided with a first set of complementary surfaces for bending said bone plate, a second set of complementary surfaces for arcing said plate, and a third set of complementary surfaces for twisting said plate, said third set being used in cooperation with a separate instrument to perform the twisting of said plate.

24. The device of claim 23, wherein the first set of complementary surfaces comprises a longitudinally extending groove flanked by bearing surfaces, in one of said jaws and a longitudinally extending ridge in the other of said jaws aligned with and opposed to the groove, so that the groove accommodates the ridge when the jaws are closed, said ridge and said bearing surfaces cooperating to apply a three point bending load on a said plate placed therebetween, upon closure of said jaws.

25. The device of claim 23, wherein the second set of complementary surfaces comprises a pair of anvils extending laterally from one of said jaws and a single anvil is provided extending laterally from said second jaw.

26. The device of claim 23, wherein the third set of complementary surfaces is comprised of flat opposed grasping surfaces on said jaws.

* * * * *